(12) United States Patent
Melcher et al.

(10) Patent No.: US 9,664,799 B2
(45) Date of Patent: May 30, 2017

(54) RADIATION DETECTOR FOR IMAGING APPLICATIONS WITH STABILIZED LIGHT OUTPUT

(71) Applicants: University of Tennessee Research Foundation, Knoxville, TN (US); Siemens Medical Solutions U.S.A., Inc., Malvern, PA (US)

(72) Inventors: Charles L. Melcher, Oak Ridge, TN (US); Mohit Tyagi, Mumbai (IN); Merry Koschan, Knoxville, TN (US); Peter Carl Cohen, Knoxville, TN (US); Matthias Schmand, Lenoir City, TN (US); Mark S. Andreaco, Knoxville, TN (US); Lars Aldon Eriksson, Oak Ridge, TN (US)

(73) Assignees: University of Tennessee Research Foundation, Knoxville, TN (US); Siemens Molecular Imaging, Malvern, PA (US)

( * ) Notice: Subject to any disclaimer, the term of this patent is extended or adjusted under 35 U.S.C. 154(b) by 4 days.

(21) Appl. No.: 14/897,881

(22) PCT Filed: Jun. 12, 2014

(86) PCT No.: PCT/US2014/042099
§ 371 (c)(1),
(2) Date: Dec. 11, 2015

(87) PCT Pub. No.: WO2014/201234
PCT Pub. Date: Dec. 18, 2014

(65) Prior Publication Data
US 2016/0124094 A1 May 5, 2016

Related U.S. Application Data

(60) Provisional application No. 61/835,072, filed on Jun. 14, 2013.

(51) Int. Cl.
*G01T 1/20* (2006.01)
*G01T 1/202* (2006.01)

(52) U.S. Cl.
CPC .......... *G01T 1/2002* (2013.01); *G01T 1/202* (2013.01); *G01T 1/2018* (2013.01); *G01T 1/2023* (2013.01)

(58) Field of Classification Search
CPC ..... G01T 1/2002; G01T 1/2018; G01T 1/202; G01T 1/2023
(Continued)

(56) References Cited

U.S. PATENT DOCUMENTS 7,723,693 B2 * 5/2010 Okada .................. G01T 1/2018
250/370.01
2005/0175254 A1 8/2005 Granfors et al.
(Continued)

FOREIGN PATENT DOCUMENTS

EP 0467044 A2 1/1992
WO 91/06875 A2 5/1991
(Continued)

OTHER PUBLICATIONS

Turner et al., "The Reduction of Response Times in Cadmium Sulphide Radiation Detectors by the use of "Biassing" Radiation", Physics in Medicine and Biology, vol. 8, No. 4, Nov. 1, 1963, pp. 439-450.

*Primary Examiner* — David Porta
*Assistant Examiner* — Carolyn Igyarto
(74) *Attorney, Agent, or Firm* — Andrews Kurth Kenyon LLP

(57) ABSTRACT

A radiation detector may include a scintillator, a light source, and a sensor. The scintillator may include various scintillation materials capable of converting non-visible radiation (incoming radiation) into visible light. The sensor may be
(Continued)

placed in adjacent or in close proximity to the scintillator, such that any converted visible light may be detected or measured by the sensor. The light source may be placed in adjacent or in close proximity to the scintillator, such that light from the light source may interact with defects in the scintillator to minimize interference on the conversion of non-visible radiation into visible light caused by the defects.

6 Claims, 4 Drawing Sheets

(58) Field of Classification Search
USPC .................. 250/365, 362, 363.09, 361 R
See application file for complete search history.

(56) References Cited

U.S. PATENT DOCUMENTS

2006/0043299 A1    3/2006  Smith et al.
2014/0107463 A1*   4/2014  Nishino ............... A61B 6/4233
                                                            600/407

FOREIGN PATENT DOCUMENTS

WO          01/08224 A1    2/2001
WO       2012/036570 A1    3/2012

* cited by examiner

100

RADIATION DETECTOR FOR IMAGING APPLICATIONS WITH STABILIZED LIGHT OUTPUT

CROSS REFERENCE TO RELATED APPLICATIONS

The present application is a U.S. National Phase of International Application No. PCT/US2014/042099, filed Jun. 12, 2014, and claims the benefit of U.S. Provisional application, Ser. No. 61/835,072, filed Jun. 14, 2013, entitled "RADIATION DETECTOR FOR IMAGING APPLICATIONS WITH STABILIZED LIGHT OUTPUT," the disclosure of which is incorporated herein by reference in its entirety.

FIELD OF THE INVENTION

The present invention is related to high-energy imaging systems and high-energy photon detectors.

BACKGROUND

Scintillation materials are scientifically and economically significant in conjunction with photodetectors to detect high-energy photons, electrons and other particles in various applications, including medical imaging, geological exploration, homeland security, and high-energy physics. In radiation detectors/imaging devices, scintillation material (for example, cerium-doped scintillators) may be used. Certain characteristics are desirable in these scintillators, in order to maximize their value in these applications. In general, high scintillation light yield, fast scintillation kinetics (both in decay time and rise time), good energy resolution, a high degree of proportionality, and relative insensitivity to ambient light exposure are desired.

To these ends, it is desirable to obtain a composition of scintillator free or relatively free of electron/hole traps and other defects that may impede the scintillation process, and/or reduce the undesirable effects of traps and defects in scintillators.

DETAILED DESCRIPTION

Figure 1:
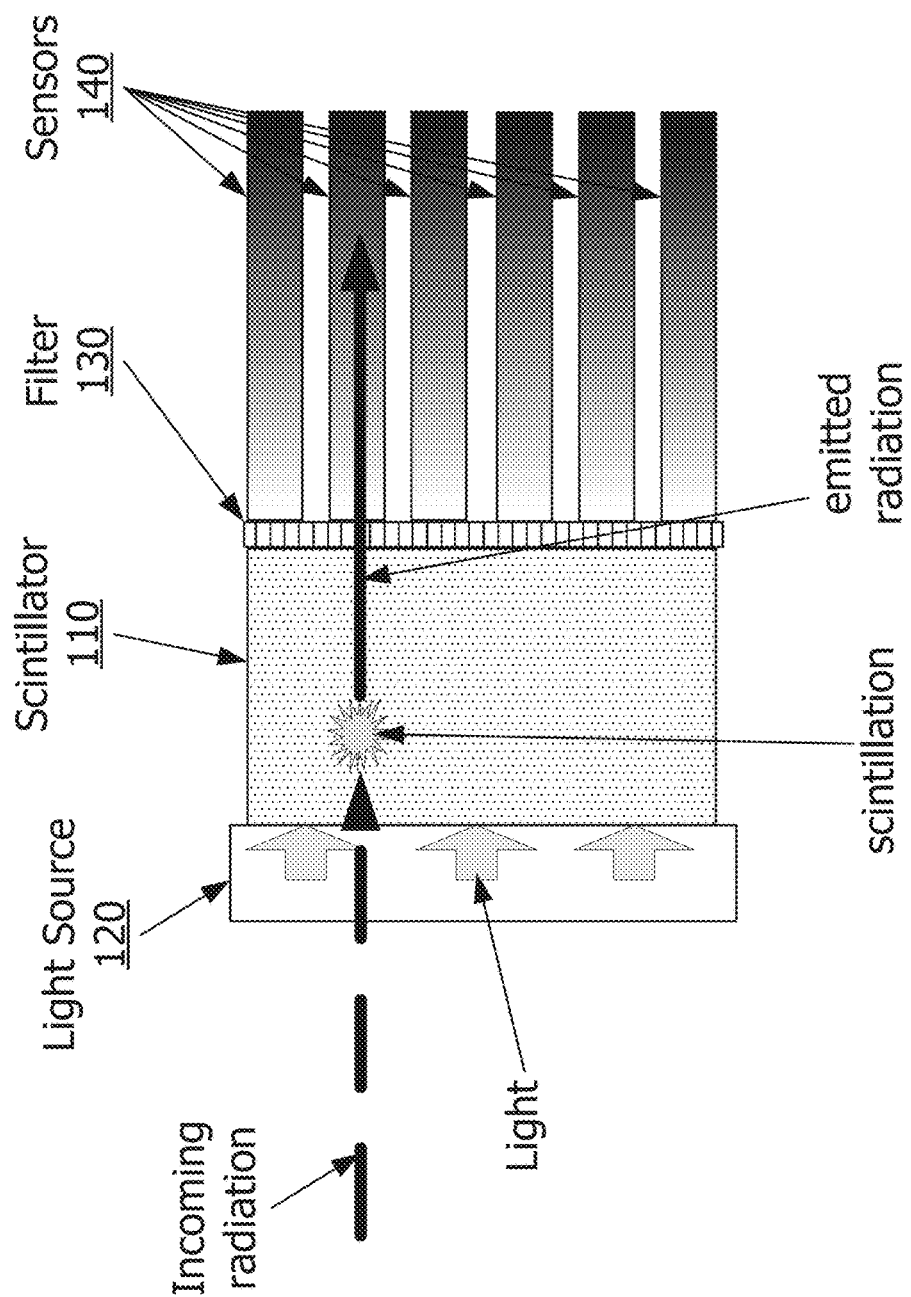
FIG. 1 illustrates a radiation detector according to an embodiment of the invention.

FIG. 1 illustrates a radiation detector 100 according to an embodiment of the invention.

According to an embodiment, the radiation detector 100 may include a scintillator 110, a light source 120, and a sensor or sensors 140.

The scintillator 110 may include various scintillation materials capable of converting non-visible radiation (incoming radiation) into visible light (emitted radiation). The sensor 140 may be placed in adjacent or in close proximity to the scintillator 110, such that any converted visible light may be detected or measured by the sensor 140. The light source 120 may be placed in adjacent or in close proximity to the scintillator 110, such that light from the light source 120 may interact with defects in the scintillator 110 to minimize interference on the conversion of non-visible radiation into visible light caused by the defects.

The scintillator 110 may be or may include a material that, when interacting with ionizing radiation, has a measurable response that may ultimately be used to produce an image. In some embodiments, the material is a scintillation material that produces photons of light when excited by the incoming radiation.

The measured quantity of light at the sensor 140 may be referred to as 'light yield' or 'light output', and is usually reported either as relative to a known standard or in absolute numbers as photons per MeV.

In some embodiments, a radiation detector 100 may be suitable for use in a variety of radiation detection applications including medical imaging applications such as positron emission tomography (PET), time-of-flight positron emission tomography (TOF-PET), X-ray computed tomography (X-ray CT) or single-photon emission computed tomography (SPECT), and any other multimodality systems (PET-CT, PET-MRI, PETSPECT).

The light source 120 may expose all portions of the scintillator 110 to light of various selected wavelengths to stabilize any longtime light output drift. The drift may be caused by the defects in the scintillation material of scintillator 110. The exposure of the scintillator 110 to light of certain wavelengths may take place inside the radiation detector 100 to maintain defects in the scintillator 110 in their saturated energy states. The saturated defects may have significantly lower influence or interference on the scintillation process. The exposure to light may be done during the normal work condition of the radiation detector 100, as well as during calibration or its idle time, continuously or intermittently or in pulses.

In some embodiments, in order to optimize performance of the radiation detector 100 for any given application, a specific light wavelength or multiple bands/ranges of wavelengths, intensity, and exposure time/duration/frequency from the light source 120 may be selected or tuned. The selection of light wavelengths, intensity, and exposure time/duration/frequency of the light source 120 may be done during design of the radiation detector 100. Alternatively, tuning of light wavelengths, intensity, and exposure time/duration/frequency of the light source 120 may be done on the fly during operation or calibration, to adjust for the performance changes, such as caused by environmental conditions. The tuning may be controlled by a controller (not shown) that controls the light source 120, and the tuning may be controlled based upon measurements of performance of the radiation detector 100.

The radiation detector 100 may further include a filter 130 between the scintillator 110 and the sensor 140, which may filter out light from the light source 120, to increase signal contrast. Because the light from the light source 120 may transmit through the scintillator 110 and reach the sensor 140, the sensor 140 may detect the light from the light source 120. The detected light from the light source 120 may be generally considered as noise. To allow the sensor 140 to detect the light from the scintillation process in the scintillator 110 and not detect (or detect less of) the light from the light source 120, the filter 130 may filter out the light from the light source 120. Since the light from the light source 120 may be tuned/selected with specific wavelengths, the filter 130 may be similarly tuned/selected to filter/block out the specific wavelengths of the light from the light source 120, such that the light from the light source 120 may be reduced in intensity after passing through the filter 130 and upon reaching the sensor 140.

In an embodiment, the light from the light source 120 may be generated by a light emitting diode (LED) or other light source of desired wavelength in the radiation detector 100 housing such that the scintillator 110 is exposed to the light from the light source 120. Or the scintillator 110 may be surrounded with a phosphor or other material that emits light at the desired wavelengths when excited by the normal emission of the scintillator itself. The light exposure should be sufficient in duration and/or intensity to saturate the defect centers in the scintillator 110, so that the defect centers are substantially incapable of trapping charge carriers and the scintillation process may be substantially unimpeded.

The light source 120 may also include a light pipe or waveguide or reflective surfaces, designed to channel light to the scintillator 110.

X-ray or other ionizing radiation sources may be implemented as part of the light source 120 into the radiation detector 100, and/or designed as a part of a x-ray generator, or radiation source. In certain embodiments of the presently disclosed subject matter, the radiation source may be removed from the vicinity of the radiation detector 100 or shielded from the radiation detector 100 to control the exposure time and amount of energy absorbed in the volume of the scintillator 110.

In an embodiment, the radiation detector 100 may expose every portion of the scintillator 110 with non-visible radiation (incoming radiation, such as x-ray) for a duration during a calibration phase, to saturate all of the defects of the scintillator 110, and then during an operation phase, the same non-visible radiation (incoming radiation, such as x-ray) may pass through a sampling material (for example a biological sample) to generate an image in the non-visible radiation, which would be detected or measured by the radiation detector 100 with saturated defects. During the calibration phase, the light source 120 may channel or direct the non-visible radiation (incoming radiation, such as x-ray) with relatively uniform intensity to every portion of the scintillator 110. During the operation phase, the light source 120's non-visible radiation may pass through the sampling material and then into the scintillator 110.

In an embodiment, the scintillator 110 may be garnet-type scintillators, such as Gadolinium Gallium garnet crystals, for example doped with Cerium (Ce) (generally referred to as GGAG or GAGG scintillators). In some embodiments, the presently disclosed subject matter incorporates gadolinium gallium garnet crystals or ceramics into the radiation detector 100 as the scintillation material. However, other material may also be used. Scintillating material compositions may include, but are not limited to, $Gd_3Ga_3Al_2O_{12}$, $Gd_3Ga_2Al_3O_{12}$, $Gd_3Ga_1Al_4O_{12}$, and other variants. These scintillators may be doped with an activator/dopant, such as cerium or praseodymium, with or without a codopant.

For initial evaluation of the potential of these gallium garnets according to the presently disclosed subject matter, cerium-doped $Gd_3Ga_3Al_2O_{12}$ (GGAG) in single-crystal form was used as an example material in the scintillator 110. However, the presently disclosed subject matter is not limited to this precise composition, nor is it limited to cerium as an activator, nor is it limited to single crystal form. Additional codopants, both aliovalent and isovalent with respect to the activator, may also be used in these compositions.

Gadolinium Gallium garnets are a promising class of scintillator 110, with high density and potentially good scintillation properties. However, materials with garnet or pervoskite structures may have vacancy defects and antisite defects, which may cause interference in the scintillation properties of these materials.

Radiation detectors, such as those used in imaging applications, may rely on consistent performance of the scintillator over the lifetime of the radiation detectors. The hardware, electronics, and software of imaging equipment is designed with the expectation that scintillator light yield will remain relatively constant within a narrow range, and deviations from this expectation may result in degraded signals or images detected.

This required consistent scintillator performance may, however, be difficult or impossible to achieve in crystalline materials alone with lattice defects, including vacancy and antisite defects.

Scintillator 110 may include materials with defect trap centers, such that the concentration of trapped charge carriers may change over time, which consequently makes the light output dependent on time, i.e. the light yield may diminish over time. This diminished light yield may cause unstable and degrading scintillator performance in medical imaging devices.

Therefore, according to some embodiments of the presently disclosed subject matter, a method and an apparatus are provided to re-saturate these traps to restore the diminished light yield by exposing the scintillator crystals to appropriate specific wavelengths of light, x-rays or any other type of ionizing radiation, creating a radiation detector 100 with stable light yield during the operations of the radiation detector 100.

In addition, some other defect trap centers may produce an afterglow effect that does not necessarily compete with the scintillation mechanism or cause a time-dependent light output, but does produce a background noise signal of additional undesirable photons in the scintillator 110. These "afterglow" defect trap centers may be filled during exposure to light of specific wavelengths. The filled "afterglow" defect trap centers may cause the afterglow effect. These defect trap centers may be emptied/detrapped by low temperature heating of the crystal or may be emptied optically, by irradiation of the crystal with certain wavelengths leading to an optical bleaching phenomena. Contrary to the trap centers that cause diminishing light output, it is preferable that the afterglow defect trap centers be empty instead of filled, to reduce the afterglow effect.

In an embodiment, the light source 120 (or a second light source near the scintillator 110) may further generate light to interact with afterglow defects in the scintillator 110 to minimize afterglow caused by the afterglow defects, by for example, tuning the light (for specific wavelengths, intensity, and duration) to empty/detrap any afterglow defects in all portions of the scintillator 110.

Figure 2:
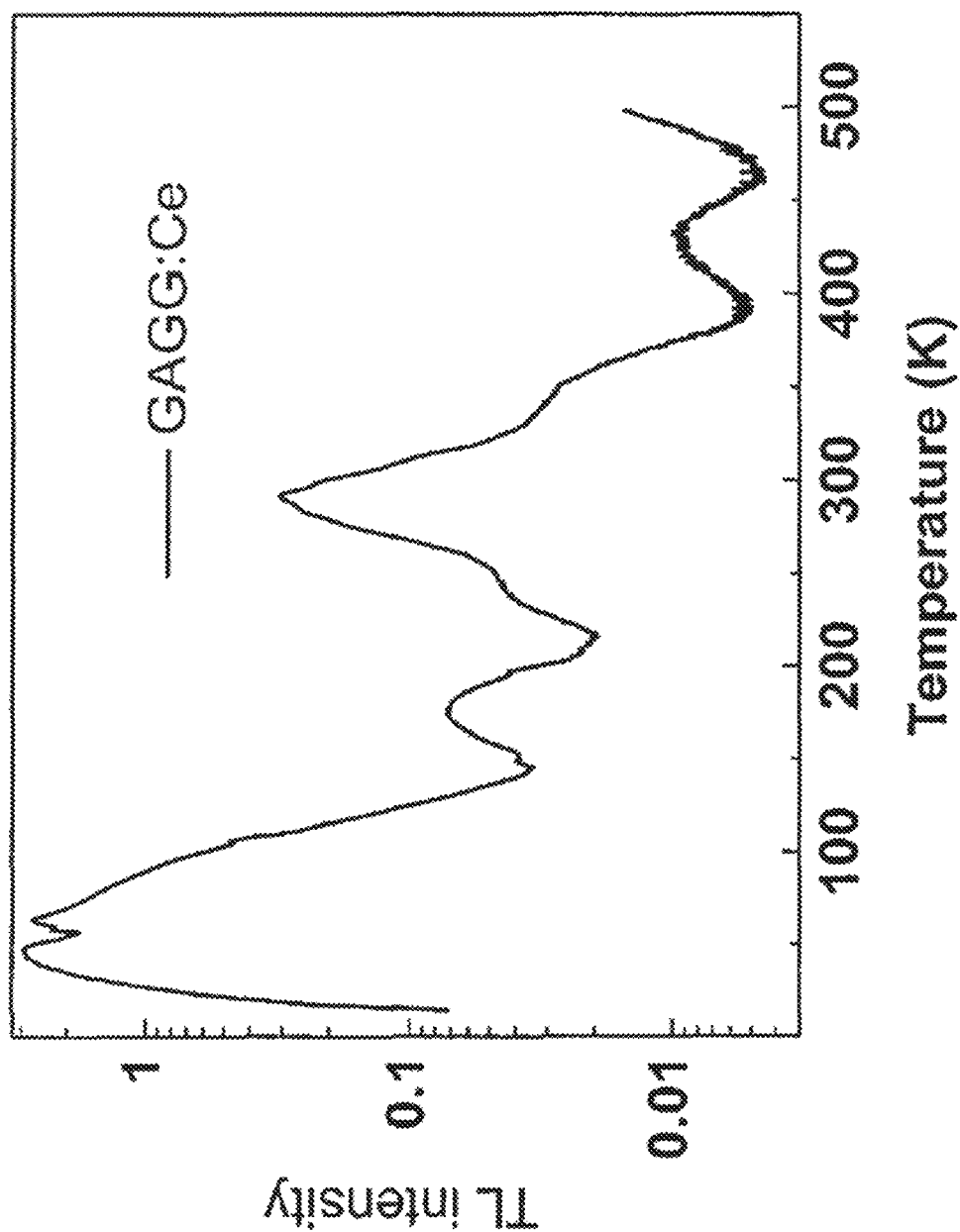
FIG. 2 illustrates characteristics of a radiation detector according to an embodiment of the invention.

FIG. 2 illustrates characteristics of a radiation detector according to an embodiment of the invention, by illustrating the thermo-luminescence (TL) glow curve of GAGG:Ce crystal in a range of temperature.

FIG. 2 shows a glow band around 300 degrees K, which may be referred to as a room temperature trap center.

The TL spectrum measured for GAGG:Ce crystals (5×5×5 $mm^3$ test sample) shows several glow bands (with glow peaks) and thus the presence of a number of trap centers from 10 degrees K to 500 degrees K. The defect trap centers responsible for the glow peaks seen at 300 K may be primarily responsible for affecting the room temperature scintillation properties in a scintillator.

The defect trap centers at room temperature may be thermally depopulated (i.e emptied/detrapped) either by heating the sample or keeping the sample in the dark for a long time. These emptied defect trap centers then may interfere with scintillation process.

During sample testing, the scintillation light output was decreased by ~45% by heating the crystal (5×5×5 mm$^3$) at 500° C. in air.

Figure 3:
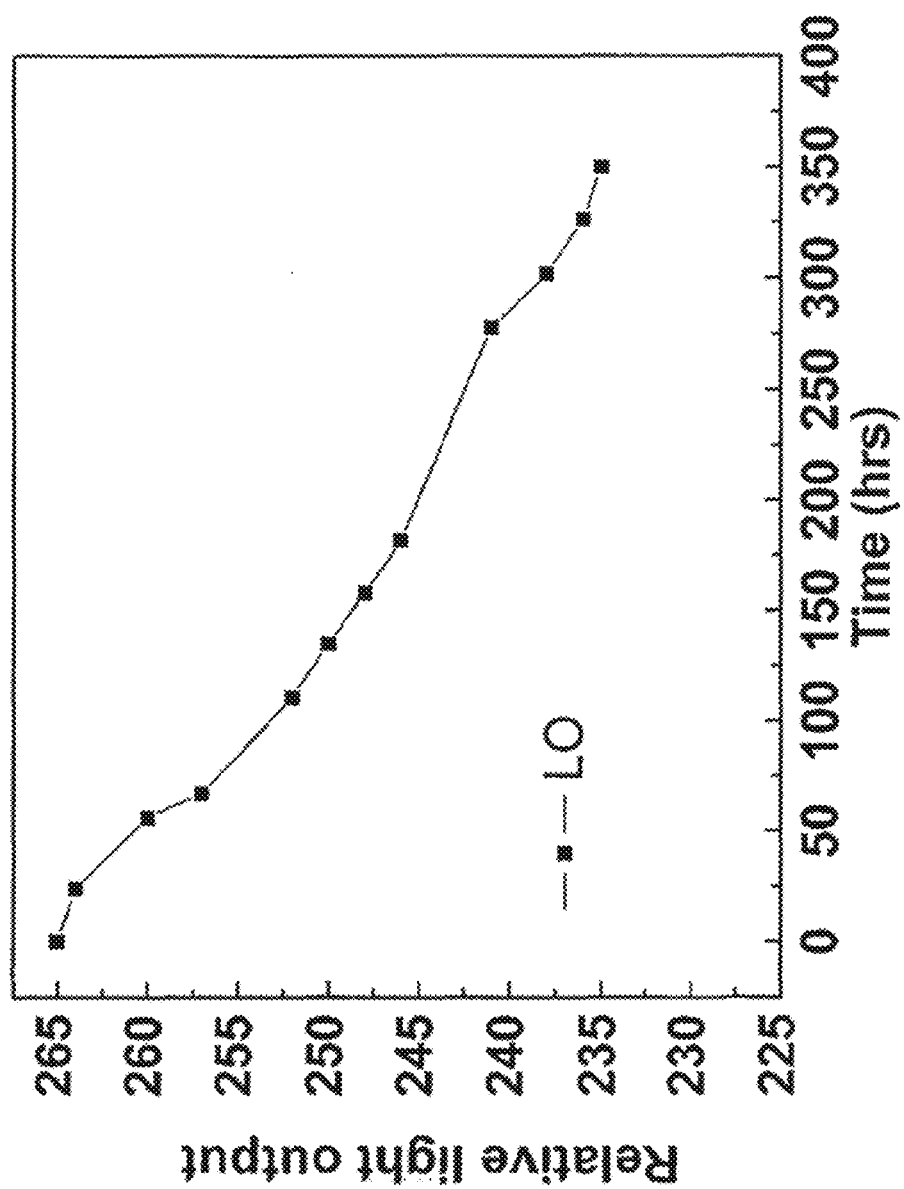
FIG. 3 illustrates characteristics of a radiation detector according to an embodiment of the invention.

The light output was also found to decrease with time by keeping the samples in the dark at room temperature as shown in FIG. 3.

FIG. 3 illustrates characteristics of a radiation detector according to an embodiment of the invention.

As illustrated in FIG. 3, keeping the crystal sample in darkness in room temperature may cause the relative light output to decrease over time. The relative light yield is presented in channel numbers in comparison to the performance of a standard Bismuth germanium oxide (BGO) crystal whose light output was set at reference channel number 100.

If not prevented, the decrease in light yield over time may lead to reduced performance in the radiation detector 100. Therefore, it is desirable to maintain the light yield at, or restore it to, the original value.

To determine the proper wavelength(s) of light from the light source 120 for restoring the light output with light exposure, the samples (5×5×5 mm$^3$) were heated at 300° C. in order to empty the charge carrier traps, reducing the measurable light yield. Subsequently, the restoration of light yield was tested by monitoring the photoluminescence (PL) emission intensity, as a representation of light yield, after the samples were exposed to light of different wavelengths.

Figure 4:
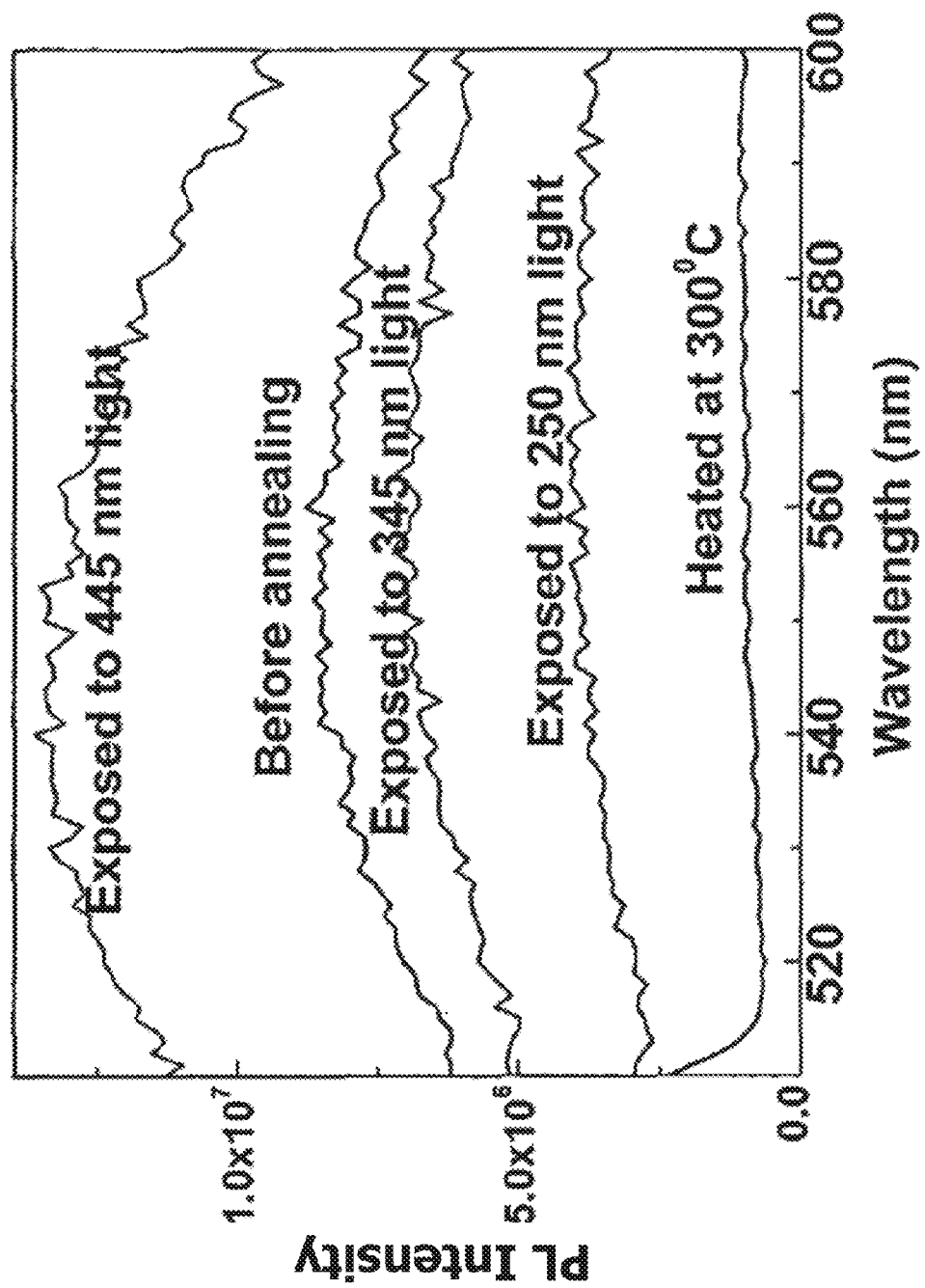
FIG. 4 illustrates characteristics of a radiation detector according to an embodiment of the invention.

FIG. 4 illustrates characteristics of a radiation detector according to an embodiment of the invention, specifically the effect of the light exposure of different wavelengths on the restoration of PL intensity after GAGG:Ce crystal samples were heated. The horizontal axis of FIG. 4 represents wavelengths of incoming radiation used to produce photoluminescence for the measurements.

As shown in FIG. 4, the PL intensity was decreased significantly in a sample after the charge carrier traps were emptied (heated at 300° C. for a duration), as compared to the "before annealing" measurements. The samples were then individually exposed to light of different wavelengths, and then tested via photoluminescence in order to observe the ability of each specific wavelength of light energy to re-fill the defect traps.

The PL emission intensity was restored to the original value after exposing the samples to light at 445 nm (from for example Ce 4$f$ energy band to 5$d$ energy band transitions) for 10 minutes.

Similarly, these results hold true for scintillation light yield by heating the crystals to 500° C., emptying the traps, and then measuring the light yield scintillation from radiation of a Cs-137 source. The measured light yield was reduced by ~45%. The crystals were then exposed to light of 445 nm wavelength for 30 minutes, and the original light yield of scintillation was restored.

Table 1 below shows the relative scintillation light output of GAGG:Ce crystal annealed at different temperatures. The light output was measured immediately after annealing without exposing the crystals to light, and then measured again after exposing the samples to ambient light for 21 hrs. The reported light yield is relative to a BGO reference standard for which the light yield was set to 100.

TABLE 1

Relative scintillation light output of GAGG:Ce crystal annealed at different temperatures

| | Before exposing to light | After exposing to light for 21 hrs |
|---|---|---|
| As grown (no anneal) | 279 | 306 |
| Annealed at 900° C. | 163 | 306 |
| Annealed at 1100° C. | 160 | 295 |
| Annealed at 1300° C. | 166 | 310 |

Therefore, a radiation detector 100 with a light source 120 which exposes the scintillator 110 with light at 345 nm or 445 nm wavelengths (which may ionize Ce$^{3+}$), may maintain substantially constant or stable light yield over the device operation lifetime by saturating defect trap centers and preventing the defect trap centers from impeding the scintillation process.

As illustrated in FIG. 4, the PL intensity measured after the samples were exposed to light of 445 nm wavelength was higher than the sample "before annealing". This is due to the contribution of TL emissions during testing.

Although the invention has been described above with reference to specific embodiments, the invention is not limited to the above embodiments and the specific configurations shown in the drawings. For example, some components shown may be combined with each other as one embodiment, or a component may be divided into several subcomponents, or any other known or available component may be added. Those skilled in the art will appreciate that the invention may be implemented in other ways without departing from the spirit and substantive features of the invention. The present embodiments are therefore to be considered in all respects as illustrative and not restrictive. The scope of the invention is indicated by the appended claims rather than by the foregoing description, and all changes that come within the meaning and range of equivalency of the claims are therefore intended to be embraced therein.

We claim:

1. A radiation detector, comprising:
a scintillator;
a light source;
a sensor, and
a filter, wherein
the scintillator is configured to convert ionizing radiation into visible light, the ionizing radiation originating externally to the radiation detector,
the sensor is configured to detect the visible light from the scintillator,
the light source is configured to expose the scintillator to a light to saturate traps in the scintillator, and
the filter is configured to prevent the light from the light source from reaching the sensor.

2. The radiation detector of claim 1, wherein the filter is between the light source and the sensor.

3. The radiation detector of claim 1, wherein the scintillator comprises a Gadolinium Gallium Aluminum garnet-based material.

4. The radiation detector of claim 1, wherein the light from the light source is one of visible, infrared, ultraviolet, X-ray, and ionizing radiation.

5. The radiation detector of claim 1, wherein the light from the light source is continuous.

6. The radiation detector of claim 1, further comprising a second light source, wherein the second light source is configured to expose the scintillator to a second light to detrap afterglow traps in the scintillator.

* * * * *